United States Patent [19]
Ross et al.

[11] Patent Number: 5,612,384
[45] Date of Patent: Mar. 18, 1997

[54] SUPERABSORBING POLYMERIC NETWORKS

[75] Inventors: Robert J. Ross, Elmhurst; Kim C. Low, Alsip; Larry P. Koskan, Orland Park, all of Ill.; Alfred P. Wheeler, Clemson, S.C.

[73] Assignee: Donlar Corporation, Bedford Park, Ill.

[21] Appl. No.: 305,266

[22] Filed: Sep. 13, 1994

[51] Int. Cl.$^6$ ............................................... C08J 9/28
[52] U.S. Cl. ............................ 521/64; 521/183; 521/184; 528/271; 528/310; 528/328; 528/335; 528/336; 528/363
[58] Field of Search ............................. 521/183, 184, 521/64; 528/271, 363, 310, 336, 328, 335

[56] References Cited

U.S. PATENT DOCUMENTS

| | | | |
|---|---|---|---|
| 5,284,936 | 2/1994 | Donachy et al. | 528/310 |
| 5,357,004 | 10/1994 | Calton et al. | 528/310 |
| 5,391,642 | 2/1995 | Wood | 528/310 |

FOREIGN PATENT DOCUMENTS

WO92/13566  8/1992  WIPO.
WO92/17525  10/1992  WIPO.

*Primary Examiner*—James J. Seidleck
*Assistant Examiner*—John M. Cooney, Jr.
*Attorney, Agent, or Firm*—Olson & Hierl, Ltd.

[57] ABSTRACT

Disclosed are methods of producing super absorbing polymeric networks of polyaspartates from crosslinked polysuccinimide. In one preferred method aspect, polysuccinimide is first reacted with an organic crosslinking agent, preferably an organic base containing at least two primary amine groups to form crosslinked polysuccinimide. The crosslinked polysuccinimide is then hydrolyzed to a polymeric network of polyaspartate which demonstrates super absorbing capability in water and in saline solution. Alternative method aspects are disclosed in which super absorbing polymeric networks of polyaspartates are produced in a single reaction vessel by sequentially crosslinking polysuccinimide with organic crosslinking agent in an aqueous reaction mixture and then hydrolyzing the reaction product to produce a polymeric network of polyaspartate.

11 Claims, 1 Drawing Sheet

SUPERABSORBING POLYMERIC NETWORKS

FIELD OF THE INVENTION

The present invention relates to the field of polymers. More particularly, the invention relates to new polymeric networks capable of absorbing large quantities of water, aqueous solutions or polar organic solvents, and methods for preparing such super absorbing polymeric networks.

BACKGROUND OF THE INVENTION

The term "water-swellable polymeric networks" as used herein refers to highly crosslinked polymers which have a propensity to swell or gel in the presence of water. Water-swellable polymeric networks have found wide use in a variety of applications. See, for example, Odian, G., *Principles of Polymerization*, 3rd Edition, published by. Wiley-Interscience, New York, 1991 and Glass, J. E., Ed. "Polymers in Aqueous Media Performance Through Association," *Advances in Chemistry Series* 223, published by the American Chemical Society, Washington, D.C., 1989).

Water-swellable polymeric networks which are well known in the polymer arts include, but are not limited to, carboxymethylcellulose, crosslinked polyacrylates, graft copolymer hydrolysis products of starch-acrylonitrile, polyvinyl alcohol resins, polyethylene oxide resins and polyacrylonitrile resins.

Several problems are associated with such polymeric networks. First, their water absorbency properties are greatly reduced in the presence of salts, such as sodium chloride, which are often present in the environments where such polymeric materials are used. Second, most of these polymeric materials are not readily biodegradable and thus contribute to the overall chemical burden on the environment when they are released into effluent streams.

Some crosslinked polypeptides containing a high percentage of anionic amino acids, such as aspartic acid or glutamic acid, are useful as super absorbing materials. Some of these are disclosed in International Patent Publication WO 92/17525 and in U.S. Pat. No. 5,284,936 to Sikes, et al. Such materials have improved saline absorbency and are biodegradable. However, they require amino acids as starting materials and these are relatively expensive.

Koskan, et al. in U.S. Pat. Nos. 5,057,597, 5,116,513, 5,219,952 and 5,221,733 describe inexpensive methods for the manufacture of polysuccinimide and polyaspartic acid. The chemical modification of polysuccinimide to produce useful polyaspartates is well known. For example, Neri, et al., in the article, "Synthesis of alpha, beta-Poly[(2-hydroxyethyl)DL-aspartamide], a New Plasma Expander," *Journal of Medicinal Chemistry*, Vol. 16, pp 893–897, (1973) describe the modification of polysuccinimide with ethanolamine.

Fujimoro et al. in U.S. Pat. No. 3,846,380 describe the formation of modified polypeptides having hydrophobic and hydrophilic substituents as side chains obtained by reacting polysuccinimide with at least one primary or secondary aliphatic amine and hydrolyzing the resulting polyamide derivative with alkali to produce polypeptides that are useful as surface active agents.

There is still a need and desire, therefore, for biodegradable, super absorbing polymeric networks with improved saline tolerance preparable by an economical method. This invention satisfies that need.

SUMMARY OF THE INVENTION

The present invention provides a method of producing super absorbing polymeric networks that are biodegradable by the chemical modification of polysuccinimide. The term "polymeric networks" as used herein refers to random copolymers of crosslinked polyaspartate which can swell or gel in water or saline solutions. The term "super absorbing polymeric networks" and grammatical variations thereof as used herein refer to polymeric networks of polyaspartates which can absorb from at least 3 times to more than 90 times their weight in water and from at least 2 times to more than 20 times their weight in aqueous 1% sodium chloride (saline solution).

The term "polyaspartate" and grammatical variations thereof as used herein, includes polyaspartic acid as well as salts of polyaspartic acid. Polyaspartates suitable for preparing super absorbing polymeric networks of the present invention can be synthesized by several methods, all of which initially involve the reaction of polysuccinimide with an organic crosslinking agent.

More particularly, one preferred method comprises reacting polysuccinimide with an organic crosslinking agent that is an organic base comprising at least two primary amine groups in an amount sufficient to form crosslinked polysuccinimide. The crosslinked polysuccinimide is subsequently hydrolyzed with base to form a crosslinked polymeric network of polyaspartate.

In one preferred method aspect, polysuccinimide is first reacted with an organic crosslinking agent in a polar aprotic solvent to crosslinked polysuccinimide. The crosslinked polysuccinimide is then collected for subsequent hydrolysis to produce a super absorbing polymeric network of polyaspartate.

Advantageously, super absorbing polymeric networks of this invention can be prepared in a single reaction vessel in alternative preferred method aspects using aqueous media. In one method aspect, polysuccinimide is crosslinked in an aqueous reaction mixture containing an effective crosslinking amount of organic crosslinking agent or salt thereof from which free organic crosslinking agent can be released by base hydrolysis to produce crosslinked polysuccinimide. The crosslinked polysuccinimide product can then be further base hydrolyzed to produce a polymeric network of polyaspartate.

The polymeric networks of the present invention are useful in a wide variety of applications, where liquid absorption, viscosity modification, chemical sequestration or dehydration is required or desired. For example, applications include the use of polymeric networks as super absorbents in diapers, incontinence products and sanitary napkins; as humectants in agricultural products; as sludge coagulants in water treatment; as viscosity modifiers in the petroleum industry; as dehydrating agents; as chemical absorbents (e.g. for clean-up of chemical spills); for controlled release of chemicals; for microencapsulation; as thickening agents; as media for electrophoresis and chromatography (e.g. for gel permeation chromatography, capillary electrophoresis, etc.); in soft contact lens manufacture; and as moisturizing components in consumer products, such as personal care products or the like.

DETAILED DESCRIPTION OF THE INVENTION

Figure 1:
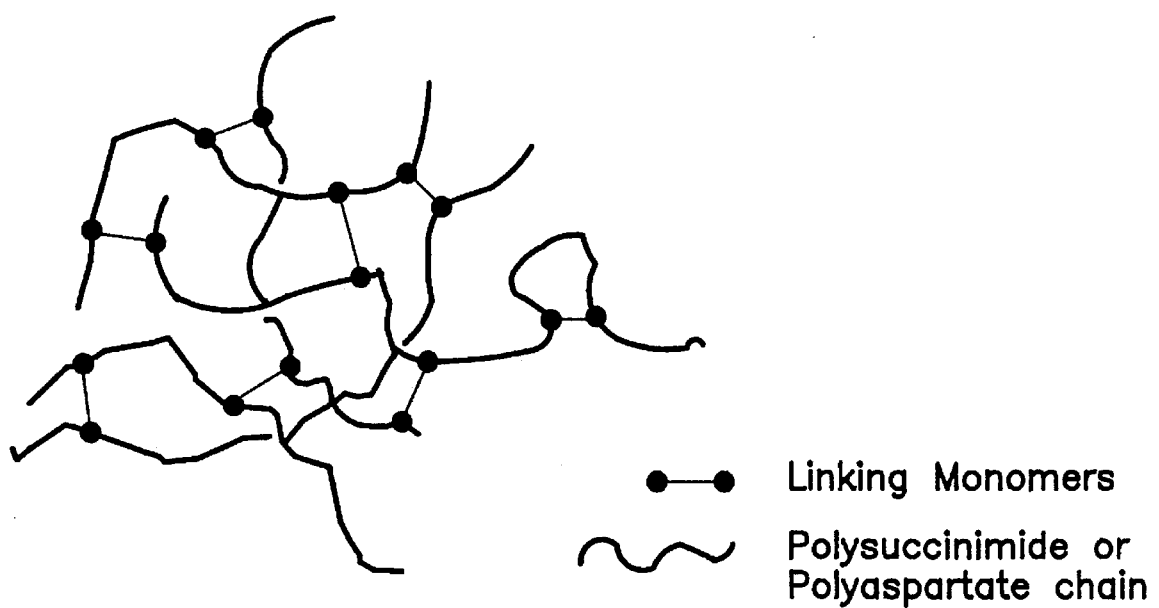
FIG. 1 is a graphic depiction of a super absorbing polymeric network embodying the principles of this invention comprised of linking monomer units, crosslinked polysuccinimide and crosslinked polyaspartate chains.

The term "polysuccinimide" as used herein defines a homopolymer having the structural formula (I), wherein n is greater than about 5.

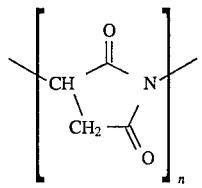

(I)

The polymeric networks of this invention are random copolymers structurally comprised of monomer units of succinimide (structural formula S), alpha-aspartate (structural formula A), beta-aspartate (structural formula B) and crosslinking dimeric aspartamides (structural formula having any one of the following three structural formulas, $L^1$, $L^2$, and $L^3$. For convenience, these will be referred to generally as structural formula (L).

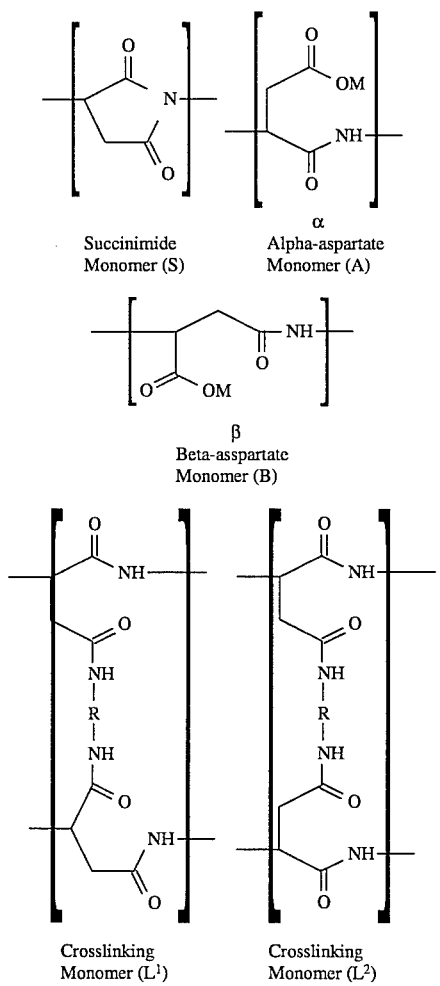

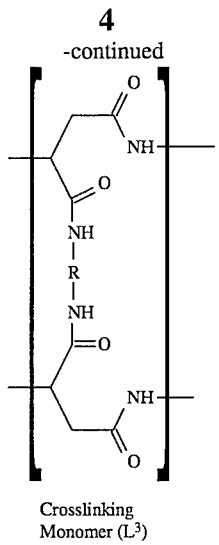

Crosslinking Monomer ($L^3$)

In the structural units, A and B, M can be hydrogen, an alkali metal cation such as $Na^+$, $K^+$ or $Li^+$, ammonium, or quaternary ammonium. In the structural L units, $L^1$, $L^2$ and $L^3$, R is a divalent organic linking group derived from the organic crosslinking agent. The organic crosslinking agent preferably is an organic base containing at least two primary amine groups capable of reacting with a succinimide monomer unit to form a crosslink thereof. For convenience, reference to "L units" includes any one of the foregoing monomeric crosslinking L structural units without limitation.

The term "crosslinked polyaspartate" or "crosslinked polyaspartic acid" as used herein refers to polymeric networks which are water-swellable and saline-swellable random copolymers structurally comprised primarily of A, B and L units. Preferably, crosslinked polyaspartates contain no S units or relatively small amount thereof, e.g., less than about 20% S units. The term "crosslinked polysuccinimide" as used herein refers to random copolymers comprised primarily of S and L units. Crosslinked polysuccinimides preferably contain no A and B units or relatively small proportions of A and B units so that the combined amount of A+B units is less than about 20%.

For convenience, the methods of this invention will be illustrated and discussed using diamine crosslinking agents. A "diamine crosslinking agent" refers herein to organic bases having two primary amine groups available for reaction with the succinimide monomer units of polysuccinimide to form a crosslink.

Useful polysuccinimide for the methods of this invention may be synthesized by any method, for example by thermal polymerization of aspartic acid, by thermal polymerization of aspartic acid in the presence of phosphoric acid or polyphosphoric acid, by thermal polymerization of maleic acid and ammonia, or any other method. Preferably, the weight average molecular weight ($M_w$) of polysuccinimide ranges from about 500 to greater than about 100,000, more preferably between about 1500 to about 50,000 and most preferably between about 5,000 and about 30,000.

The amount of the diamine crosslinking agent preferably ranges from about 0.001 moles to about 5 moles per kilogram of succinimide. Using a formula weight (FW) of 97 for polysuccinimide (the formula weight of a succinimide monomer unit), the amount of organic diamine component can also be expressed as moles of diamine per mole of succinimide monomer units×100%, hereafter referred to as "mol %". On this basis, the amount of diamine crosslinking agent can range from a mol % of about 0.1 to about 50.

The preferred mol % of diamine is dependent upon the weight average molecular weight ($M_w$) of the polysuccinimide starting material. For polysuccinimides of $M_w$ between about 500 and about 4000, the preferred mol % amount of diamine crosslinking agent is from about 10 to about 30. For polysuccinimides of $M_w$ between about 4000 to about 10,000, the preferred mol % amount of diamine crosslinking agent is about 1 to about 20 mol %. For polysuccinimides of $M_w$ greater than about 10,000 the preferred mol % amount diamine crosslinking agent is from about 0.5 to about 15.

The crosslinking can occur between adjacent polymer chains or within the same polymer chain or both. Multiple crosslinks can also be incorporated into the polymer chains.

Compounds useful as diamine crosslinking agents in practicing the methods of the present invention include, but are not limited to, aliphatic diamines, such as ethylenediamine (EDA), 1,3-bis(aminoethyl)cyclohexane (1,3-BAC), and hexamethylene diamine (HMDA); arylaliphatic diamines, such as meta-xylylene diamine (MXDA); and polyether diamines, such as polyoxyalkylenediamines and amine terminated block copolymers of polyoxyalkylene/ polyalkylene glycols, sold in varying approximate molecular weights ranging from about 280 to about 2,000 under the trademark JEFFAMINE™ by Texaco Chemical Company.

According to the supplier, the JEFFAMINE™ D series products are amine terminated polypropylene glycols having an average of from about 2 to about 68 propylene oxide units, the JEFFAMINE™ ED series of products are amine terminated polyethylene/polypropylene glycols, having a predominantly polyethylene oxide backbone and the following general structural formula (II) where the average approximate value of the a+c structural units is about 2.5 and that of the b structural unit is from about 8 to about 40.5.

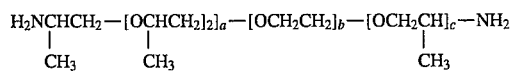

Other useful polyether amines are triethyleneglycol diamine (JEFFAMINE™ EDR-148) and tetraethyleneglycol diamine (JEFFAMINE™ EDR-192).

Also useful are amine terminated polyalkyleneimines, such as amine terminated polyethyleneimines including, for example, triamines and pentamines, such as diethylenetriamine (DETA) and tetraethylenepentamine (TEPA).

Additionally, triamino, tetraamino and polyamino organic compounds can also be used as organic crosslinking agents to form new polymeric networks of the present invention. The use of such amino compounds can further lead to incorporation of linking monomer units such as the following $L^4$ and $L^5$ structural formulas, where $R^2$ is a trivalent or tetravalent organic radical linking group derived from the organic crosslinking agent.

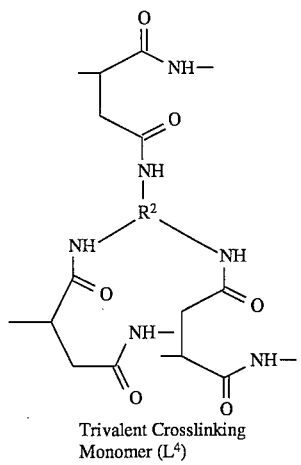
Trivalent Crosslinking Monomer ($L^4$)

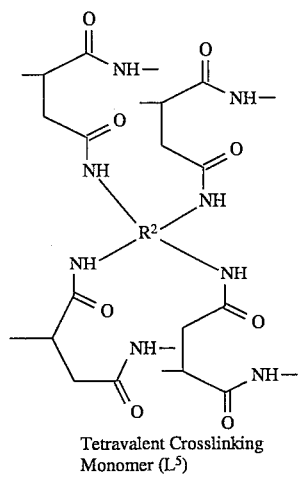
Tetravalent Crosslinking Monomer ($L^5$)

Examples of triamino, tetraamino and polyamino compounds useful as organic crosslinking agents in the present invention include, but are not limited to tris(2-aminoethyl)amine (TAEA), polyamine compounds sold under the trademark STARBURST™ Dendrimers by Dendritech, Inc., the propylene oxide based triamine series sold in various approximate molecular weights ranging from about 440 to about 5,000 under the trademark JEFFAMINE™ T by Texaco Chemical Company, and polyvinylamine polymers.

Aromatic diamines, such as meta-phenylenediamine, hydrazine, carbohydrazine and other bis-hydrazides were found less effective as organic crosslinking agents in the present invention.

Preferably, super absorbing polymeric networks of the present invention swell or gel in the presence of water to from at least 3 times to over 90 times their dry weight, and in the presence of saline, such as aqueous 1% sodium chloride (NaCl), to from at least 2 times to over 20 times their dry weight.

Briefly described, in one preferred method aspect, polymeric networks of crosslinked polyaspartates were produced by first crosslinking polysuccinimide with an organic crosslinking agent in the presence of a polar aprotic solvent. The crosslinked polysuccinimide product was then isolated from the reaction mixture, collected and hydrolyzed to a polymeric network gel comprising polyaspartate. The gel can then be dried for use as a super absorbing polymeric network.

Useful polar aprotic solvents include dimethylsulfoxide, dimethylformamide and dimethylacetamide but are not limited thereto. Preferably, the aprotic solvent is at least water-miscible. The crosslinked polysuccimimide product is preferably isolated by admixing the reaction mixture with a polar solvent, preferably water or an alcohol, in which the polar aprotic solvent is soluble but in which the crosslinked polysuccinimide product is not soluble to precipitate the polymer. The precipitated crosslinked polysuccinimide polymer can then be collected for hydrolysis to a super absorbing polymeric network of polyaspartate.

In alternative method aspects, a super absorbing polymeric network of polyaspartate can be produced in an aqueous reaction mixture using a single reaction vessel.

For example, an aqueous solution of organic crosslinking agent is first neutralized with a sufficient amount of a relatively strong mineral acid, preferably hydrochloric acid, to form a water-soluble acid salt thereof. Next, polysuccinimide is admixed therein to form a slurry with the salt solution. The polysuccinimide is subsequently crosslinked by adding sufficient aqueous sodium hydroxide to release a crosslinking amount of free organic crosslinking agent in the reaction mixture to produce crosslinked polysuccinimide. The crosslinked polysuccinimide product is then further base hydrolyzed to a super absorbing polymeric network of polyaspartate.

In another method aspect, polysuccinimide can be slurried in water and the slurry admixed with an effective crosslinking amount of organic crosslinking agent to produce crosslinked polysuccinimide, which is then further base hydrolyzed to a super absorbing polymeric network of polyaspartate.

The following examples illustrate the preparation of embodiments of super absorbing polymeric networks of polyaspartates from crosslinked polysuccinimide by the methods discussed. The examples and methods presented are illustrations of preferred embodiments and are not intended as limitations.

Preparation of Crosslinked Polysuccinimide (Method A)

To illustrate the methods of this invention, crosslinked polysuccinimide described in examples 1–17 were synthesized by the following general method referred to as Method A.

Polysuccinimide of a given $M_w$ is dissolved in polar aprotic solvent about 10 mL solvent/gram, for example, dimethylsulfoxide (DMSO) or dimethylformamide (DMF), as indicated below. A selected mol % of diamine crosslinking agent was then added. The reaction mixture can be heated to accelerate the crosslinking reaction. Preferably, the temperature of the reaction mixture was in the range of from about 25° C. to about 60° C., more preferably in the range of from about 45° C. to about 50° C. The resulting crosslinked polysuccinimide product was generally in the form of a gel or a solid precipitate. This product was then isolated by pouring the reaction mixture into a solvent, such as water or an alcohol, in which the polar aprotic solvent is soluble, but in which the polymer is not. This produced a solid or precipitate, which can be isolated by filtration and dried.

Example 1: Synthesis of Crosslinked Polysuccinimide by Method A

As shown in Table 1, polysuccinimide having a $M_w$ of about 5100 (about 9.78 g, 100 mmol of succinimide units) was dissolved in DMSO solvent (about 100 mL) at a temperature of about 40° C. Ethylenediamine (EDA) (about 1 g, 10 mmol) was then added with stirring over a period of about 5 minutes at a temperature of from about 45° C. to about 50° C. A gelatinous reaction mixture of crosslinked polysuccinimide formed after a few minutes.

Next, the gelatinous reaction mixture was heated at a temperature of about 50° C. for about an additional 2 hours to ensure complete reaction. The gelatinous reaction mixture was then cooled to about ambient temperature. The cooled reaction mixture was poured into about 600 mL of methanol with stirring. A pinkish-tan colored precipitate was produced. The product was collected by filtration and substantially dried at about 70° C. The yield was about 10.2 grams.

Examples 2–17: Syntheses of Crosslinked Polysuccinimides

Other examples of crosslinked polysuccinimides successfully made by following the method of Example 1, except that the diamine crosslinking agent, mol % amount thereof, polysuccinimide of given $M_w$ and solvent employed were as listed in Table 1.

TABLE 1

CROSSLINKED POLYSUCCINIMIDES

| Example | Diamine[1] | Polysuccinimide Mol. Wt ($M_w$) | Mol % Diamine | Solvent[2] |
|---------|-----------|-------------------------------|---------------|-----------|
| 1 | EDA | 5100 | 10 | DMSO |
| 2 | EDA | 5100 | 5 | DMSO |
| 3 | EDA | 5100 | 15 | DMSO |
| 4 | MXDA | 5100 | 7 | DMSO |
| 5 | EDA | 5100 | 10 | DMF |
| 6 | MXDA | 5100 | 11 | DMSO |
| 7 | 1,3-BAC | 5100 | 7 | DMF |
| 8 | 1,3-BAC | 5100 | 11 | DMF |
| 9 | EDR-148 | 5100 | 10 | DMF |
| 10 | EDR-148 | 5100 | 15 | DMF |
| 11 | EDR-48 | 5100 | 20 | DMF |
| 12 | MXDA | 5100 | 15 | DMF |
| 13 | DETA | 5100 | 10 | DMF |
| 14 | TAEA | 5100 | 10 | DMF |
| 15 | EDA | 1500 | 20 | DMF |
| 16 | EDR-148 | 30,000 | 13 | DMSO |
| 17 | EDA | 30,000 | 4 | DMF |

Notes To Table 1
[1]Diamine = diamine crosslinking agent
MXDA = metaxylylenediamine
EDA = ethylenediamine
1,3-BAC = 1,3-bis(aminomethyl)cyclohexane
EDR-148 = triethyleneglycol diamine, approximate molecular weight 148 (JEFFAMINE ™ EDR-148, Texaco Chemical Company)
DETA = diethylenetriamine
TAEA = tris(2-aminoethyl)amine
[2]DMSO = dimethylsulfoxide
DMF = dimethylformamide Preparation of Polymeric Networks of Crosslinked Polyaspartate (Method B)

In Examples 18–23 and 25–29, polymeric networks of crosslinked polyaspartate Examples were synthesized by Method B, described generally as follows.

A crosslinked polysuccinimide was first prepared by the general Method A discussed above. The crosslinked polysuccinimide was then suspended in a sufficient quantity of aqueous sodium hydroxide solution to theoretically completely hydrolyze the polysuccinimide and any remaining succinimide units in the polymer to produce an aqueous gel of crosslinked polyaspartate. The pH of the resulting aqueous polymeric network gel was then adjusted to whatever value was desired.

The gel can be substantially dried to a solid at this point, or alternatively, it can be diluted with excess water and washed or dialyzed before the drying step.

Example 18: Synthesis of a Polymeric Network of Crosslinked Polyaspartate by Method B A polymeric network of polyaspartate, as shown in Table 2, was prepared from polysuccinimide having a $M_w$ of about 5100 (30 mmol succinimide units) crosslinked by the procedure of Method A with 15 Mol % MXDA. The crosslinked polysuccinimide (about 6 g) was admixed with about 30 mL aqueous 1N sodium hydroxide (30 mmol) to a slurry of crosslinked polysuccinimide. A gel reaction mixture formed in about 1 minute. Next, water (about 50 mL) was added to make the gel reaction mixture stirrable.

The gel reaction mixture was heated with stirring at about 50° C. for about 4 hours. The initial pH was 12.6. After about 4 hours, the pH was about 10.8. Next, the gel reaction mixture was allowed to stand at ambient room temperature for about 20 hours. The pH was then adjusted to about 9.5 with about 4 mL of 1N HCl. A polymeric network gel was produced, which was allowed to settle. The supernatant liquid was decanted off and the gel was then substantially dried at about 50° C. for about 24 hours. A tan solid was produced. The yield was about 5.9 grams.

Examples 19–23 and 25–29: Additional Syntheses

Other polymeric networks of polyaspartates were successfully synthesized by Method B by following the procedure of Example 18 except that the polysuccinimide, diamine crosslinking agent, mol % amounts and pH values employed were as listed in Table 2.

TABLE 2

CROSSLINKED POLYASPARTATES

| Example | Diamine[1] | Polysuccinimide Mol. Wt. ($M_w$) | Mol % Diamine | pH | Method |
|---|---|---|---|---|---|
| 18 | MXDA | 5100 | 15 | 9.5 | B |
| 19 | EDA | 5100 | 10 | 4.0 | B |
| 20 | EDA | 5100 | 10 | 3.8 | B |
| 21 | EDA | 5100 | 15 | 4.0 | B |
| 22 | EDA | 5100 | 10 | 9.5 | B |
| 23 | EDA | 5100 | 15 | 9.3 | B |
| 24 | HMDA | 5000 | 15 | 10 | D |
| 25 | 1,3-BAC | 5100 | 11 | 9.5 | B |
| 26 | EDR-148 | 5100 | 15 | 9.7 | B |
| 27 | EDR-148 | 5100 | 20 | 9.5 | B |
| 28 | DETA | 5100 | 10 | 9.5 | B |
| 29 | TAEA | 5100 | 10 | 9.5 | B |
| 30 | EDA | 30000 | 5 | 8.5 | C |
| 31 | EDA | 1500 | 20 | 9.5 | C |
| 32 | EDA | 30000 | 4 | 9.5 | C |
| 33 | EDR-148 | 30000 | 13 | 9.5 | C |
| 34 | EDR-148 | 5000 | 30 | 10 | D |
| 35 | HMDA | 5000 | 7 | 10 | D |
| 36 | HMDA | 5000 | 10 | 10 | D |

Notes to Table 2
[1]Diamine = diamine crosslinking agent (See identifying note 1 to Table 1). HMDA = hexamethylenediamine Preparation of Polymeric Networks of Polyaspartate (Method C)

Examples 30–33 illustrate the preparation of polymeric networks of polyaspartate by an alternative method embodiment referred to as Method C. First, polysuccinimide of a given $M_w$ was dissolved in a polar aprotic solvent and a diamine crosslinking agent was added to form crosslinked polysuccinimide generally as described in Method A. The mixture can be heated to ensure complete reaction.

When a gel or solid suspension was produced, it was then diluted with a sufficient quantity of aqueous sodium hydroxide solution to completely hydrolyze the crosslinked polysuccinimide and any remaining succinimide monomer units of the polymer. After completion of the hydrolysis to a polymeric network of polyaspartate, the pH can be adjusted to any value desired.

The resulting polymeric network gel of polyaspartate was then separated from the supernatant fluid by decanting or centrifuging, to remove substantially most of the polar aprotic solvent. The gel was then washed or dialyzed with water to remove any remaining solvent. This produced a water-swollen polymeric network gel.

The water-swelled polymeric network gel was then substantially dried to a solid.

Example 30: Synthesis of Polymeric Networks of Polyaspartate by Method C

As shown on Table 2, a polymeric network of polyaspartate was prepared from a crosslinked polysuccinimide prepared generally by Method A as follows. Polysuccinimide was crosslinked by adding ethylenediamine (EDA) (0.25 g, 2.5 mmol) over a period of about 3 minutes to a solution of polysuccinimide of Mw of about 30,000 (5.0 g, about 50 mmol succinimide units) in about 50 mL of DMF solvent at a temperature ranging from about 45° C. to about 50° C. Within minutes, a substantially clear, firm gel was produced. This gel product was allowed to stand at about 50° C. for about one hour and then cooled to about ambient room temperature. The cooled gel product was allowed to stand at room temperature for about an additional 2 hours.

Next, a polymeric network of polyaspartate was prepared as follows. The gel product was cut up into fine shards and suspended, with stirring, in 1N NaOH solution (42 mL, 42 mmol) at about 45° C. to about 50° C. Initially, the pH was about 12.9. After about 3 hours, the pH had dropped to about 8.5. A gelatinous solid was produced. The supernatant liquid was then poured off and the gelatinous solid was diluted with about 180 mL of water. A polymeric network gel formed and considerable water swelling of the gel was observed. Excess water was then removed from the water-swollen gel by filtering through a 200 mesh wire sieve.

The water-swollen gel was then diluted with about 100 mL of water and again filtered and the resulting water-swollen polymeric network gel collected. The weight of the water-swollen polymeric network gel was determined to be about 156 grams.

The water-swollen polymeric network gel was then dried at about 70° C. for about 20 hours to afford about 6.85 grams of an off white solid. On the basis of this yield, the water content of the water-swollen polymeric network gel had represented about 23 times the weight of the dry polymeric network.

Examples 31–33: Preparation of Polymeric Networks of Polyaspartate by Method C

Other polymeric networks of polyaspartates were successfully synthesized by Method C by following the procedure of Example 30 except that the polysuccinimide, diamine crosslinking agent, mol % amounts and pH values employed were as listed in Table 2.

Preparation of Polymeric Networks of Polyaspartate (Method D)

Examples 24 and 34–36 illustrate the preparation of polymeric networks of polyaspartate by another alternative method embodiment referred to as Method D. First, an aqueous salt solution of organic diamine crosslinking agent was prepared by adding the organic diamine crosslinking agent to water and neutralizing it with hydrochloric acid to form the hydrochloride salt thereof. Polysuccinimide of a selected $M_w$ was then added to form a slurry. Aqueous sodium hydroxide was then added in an amount calculated to neutralize the diamine hydrochloride and generate a crosslinking amount of the free diamine crosslinking agent to react with the polysuccinimide and form crosslinked polysuccinimide.

Next, additional aqueous sodium hydroxide was added in an amount sufficient to hydrolyze the crosslinked polysuccinimide and any remaining succinimide monomer units in the polymer. A polymeric network gel was produced. The polymeric network gel can then be collected and substantially dried.

A variation of this method can be practiced by adding the free diamine crosslinking agent to an aqueous slurry of polysuccinimide, followed by addition of the aqueous sodium hydroxide solution as described above.

Example 34: Synthesis of polymeric Networks of Polyaspartate by Method D

Triethylenegolycol diamine (EDR-148) (about 100 g, 0.67 mol) was acidified with 6N HCl solution to a final pH of about 1.7. The final total weight of the solution was about 305.53 g. Polysuccinimide (about 20 g, 200 mmol of succinimide units, Mw about 5000) and water (about 10 mL) were combined with about 28.84 g (60 mmol) of the neutralized diamine and the mixture was stirred vigorously to form a slurry. Aqueous sodium hydroxide (about 50%) solution was added dropwise at a rate of about 1 mL per min until gel formation occurred (approximately 15 min.). The gel was dried at about 70° C. for about 48 hours and then ground to a powder. The yield was about 26 g.

Examples 35–36: Syntheses of Polymeric Networks of Polyaspartates by Method D

Other polymeric networks of polyaspartates were successfully synthesized by following the method of Example 34 except that the polysuccinimide, amine crosslinking agent and Mol % of amine crosslinking agent employed were as listed in Table 2.

Example 37: Super Absorbing Polymeric Networks of Polyaspartates

The super absorbing characteristics of each of the polymeric networks of crosslinked polyaspartate of Examples 18–36 was demonstrated by the values obtained in the following protocol employing either deionized water or aqueous 1% sodium chloride (saline solution).

Approximately 100 milligrams (mg) of polymeric network of polyaspartate was added into a pre-weighed test tube. An amount of either deionized water or saline solution was added in sufficient excess the contents of the tube to swell the polymeric network and provide supernatant liquid. The tube was then allowed to stand undisturbed for about 25 minutes, at the end of which time, the tube was centrifuged at about 1500 rpm for about 5 minutes. The supernatant liquid was then removed by pipette.

The tube with its contents was then weighed and the amount of liquid that had been absorbed by the polymeric network was determined. Water absorbency or saline absorbency was expressed as the ratio of the weight of the water swollen or saline swollen polymeric network gel divided by its weight when dry. Each evaluation was made in triplicate and an average value calculated.

The average values for the data obtained for water absorbency and for saline absorbency are compared in Table 3 for the polymeric networks of crosslinked polyaspartates of Examples 18–36. Also shown is the approximate ratio of the value for saline absorbency to water absorbency.

TABLE 3

WATER AND SALINE ABSORBENCY FOR CROSSLINKED POLYASPARTATES

| Polymeric Network | A Water Absorbency | B Saline Absorbency | Ratio B:A Absorbency |
|---|---|---|---|
| Ex. 18 | 10.5 | 7.4 | 0.7 |
| Ex. 19 | 5.6 | 4.6 | 0.8 |
| Ex. 20 | 8.9 | 5.8 | 0.7 |
| Ex. 21 | 5.5 | 4.0 | 0.7 |
| Ex. 22 | 16.9 | 9.3 | 0.6 |
| Ex. 23 | 8 | 5.3 | 0.7 |
| Ex. 24 | 3.7 | 3.7 | 1 |
| Ex. 25 | 13.1 | 7.9 | 0.6 |
| Ex. 26 | 14.6 | 6.2 | 0.4 |
| Ex. 27 | 8.3 | 5.8 | 0.7 |
| Ex. 28 | 8.6 | 8.3 | 1 |
| Ex. 29 | 6.9 | 5.6 | 0.8 |
| Ex. 30 | 28.3 | 13.5 | 0.5 |
| Ex. 31 | 5.7 | 4.4 | 0.8 |
| Ex. 32 | 71.3 | 21.4 | 0.3 |
| Ex. 33 | 93 | 23.4 | 0.3 |
| Ex. 34 | 4.2 | 4 | 1 |
| Ex. 35 | 3.1 | 2.9 | 1 |
| Ex. 36 | 5.2 | 5.3 | 1 |

As shown by the water absorbing data in Table 3, all of the polymeric networks absorbed from at least about 3 times their weight to over 90 times their weight in water. As generally observed with all known water-swellable polymers, water absorbency decreased with increasing ionic strength of the solution. Thus, the overall absorbency generally is reduced in saline solution compared to that of in water. Surprisingly, however, the water and saline absorbency of the polymeric networks of Examples 24, 28, 34, 35 and 36 were substantially similar as shown by the ratio of saline absorbency to water absorbency data.

By contrast, it was noted while practicing Method A, that the crosslinked polysuccinimides of Examples 1–17 did not swell in aqueous solutions, but did swell in the presence of polar organic solvents.

It is known from the art that for most polyacrylate based absorbents, the degree to which water absorbency is decreased by the presence of salts is quite large. Generally, the absorbency of 1% sodium chloride solution is less than about 20% of pure water absorbency. Thus, the water absorbing properties of the polymeric networks of the present invention are less sensitive to the presence of salts, as evidenced by the ratio of the saline absorbency to water absorbency in Table 3.

What is claimed is:

1. A method of producing polymeric networks comprising crosslinked polyaspartate comprising the steps of:

a) dissolving a polysuccinimide in a polar aprotic organic solvent;

b) reacting the dissolved polysuccinimide with an effective crosslinking amount of an organic crosslinking agent that is an organic base containing at least two primary amine groups to form a crosslinked polysuccinimide product in the resulting reaction mixture;

c) isolating the crosslinked polysuccinimide product obtained by admixing the reaction mixture with a solvent in which the polar aprotic organic solvent is soluble and the crosslinked polysuccinimide product is not;

d) recovering the crosslinked polysuccinimide product; and e) hydrolyzing the recovered crosslinked polysuccinimide product to produce a polymeric network of polyaspartate.

2. The method of claim 1 wherein the reaction mixture in step (b) is heated to a temperature range of from about 25° C. to about 60° C. and maintained at said temperature range until the crosslinked polysuccinimide product forms.

3. The method of claim 2 further including the step of cooling the reaction mixture to ambient room temperature between step (b) and step (c).

4. The method of claim 1 wherein the crosslinked polysuccinimide is collected in step (d) by filtering and drying the crosslinked polysuccinimide.

5. The method of claim 1 further including the step of collecting the polymeric network of polyaspartate.

6. The method of claim 5 further including the step of substantially drying the polymeric network.

7. The method of claim 1 wherein the polymeric network of polyaspartate is in the form of a gel or solid.

8. The method of claim 1 wherein the polysuccinimide in step (a) has a weight average molecular weight in the range of from about 500 to greater than about 100,000.

9. The method of claim 1 wherein the amount of organic crosslinking agent based on moles of diamine per mole of succinimide monomer units in the polysuccinimide is present in a mol % amount of about 0.1 to about 50.

10. The method of claim 1 wherein the polysuccinimide in step (a) has a weight average molecular weight in the range of from about 500 to greater than about 100,000 and the organic crosslinking agent based on moles diamine per mole of succinimide monomer units in the polysuccinimide is present in a mol % amount of about 0.1 to about 50.

11. A super absorbing polymeric network of polyaspartate obtained by the method of claim 1 characterized as a random copolymer comprised primarily of succinimide units and dimeric aspartamide units with less than about 20% aspartate units in alpha form, beta form or both.

* * * * *